United States Patent
Kim et al.

(10) Patent No.: US 9,314,393 B2
(45) Date of Patent: Apr. 19, 2016

(54) ACTIVE ROBOTIC GAIT-TRAINING SYSTEM AND METHOD

(75) Inventors: Young Ho Kim, Gangwon-do (KR); Sung Jae Hwang, Seoul (KR); Jong Sang Son, Gyeongsangnam-do (KR); Jung Yoon Kim, Gyeonggi-do (KR); Sun Woo Park, Gangwon-do (KR); Je Seong Ryu, Gangwon-do (KR); Min Hyeon Lee, Daejeon (KR)

(73) Assignee: Yonsei University Wonju Industry-Academic Cooperation Foundation, Wonju-si, Gangwon-do (KR)

(*) Notice: Subject to any disclaimer, the term of this patent is extended or adjusted under 35 U.S.C. 154(b) by 205 days.

(21) Appl. No.: 14/007,340
(22) PCT Filed: Apr. 9, 2012
(86) PCT No.: PCT/KR2012/002678
§ 371 (c)(1),
(2), (4) Date: Dec. 3, 2013
(87) PCT Pub. No.: WO2012/138203
PCT Pub. Date: Oct. 11, 2012

(65) Prior Publication Data
US 2014/0094345 A1 Apr. 3, 2014

(30) Foreign Application Priority Data
Apr. 8, 2011 (KR) .................. 10-2011-0032679

(51) Int. Cl.
*A63B 24/00* (2006.01)
*A63B 71/00* (2006.01)
(Continued)

(52) U.S. Cl.
CPC ........ *A61H 1/0255* (2013.01); *A63B 21/00178* (2013.01); *A63B 21/00181* (2013.01);
(Continued)

(58) Field of Classification Search
CPC .............. A61H 1/0255; A61H 1/0262; A61H 2201/163; A61H 2201/5069; A61H 2201/1642; A61H 2201/10; A61H 1/00; A61H 1/02; A61H 1/0237; A61H 1/0244; A61H 1/0259; A61H 1/0266; A61H 3/00; A61H 2001/027; A61H 2003/007; A61H 2201/1628; A61H 2201/164; A61H 2203/00; A61H 2203/04; A61H 2203/0406; A61H 2205/088; A61H 2205/10; A61H 2205/102; A61H 2205/106; A61H 2205/108; A63B 69/0064; A63B 71/0009; A63B 21/00178; A63B 21/00181; A63B 21/1423; A63B 21/1419; A63B 2213/004; A63B 2220/16; A63B 2022/0094; A63B 22/0235; A63B 21/0058; A63B 21/0059; A63B 21/4047; A63B 21/4049; A63B 23/04; A63B 23/0405; A63B 23/0417; A63B 23/0423; A63B 23/0429; A63B 23/0458; A63B 23/0464; A63B 23/047; A63B 23/0476; A63B 23/0482; A63B 23/0488; A63B 23/0494; A63B 23/08; A63B 23/10; A61N 1/36014; A61N 1/36003
USPC ......... 482/1–8; 602/23; 601/5, 23–24, 33–35; 623/40
See application file for complete search history.

(56) References Cited

U.S. PATENT DOCUMENTS
2,010,482 A * 8/1935 Cobb ............................. 623/31
6,666,831 B1 * 12/2003 Edgerton et al. .............. 600/587
(Continued)

FOREIGN PATENT DOCUMENTS
| JP | 2004-201892 A | 7/2004 |
|---|---|---|
| JP | 2005-074063 A | 3/2005 |
| JP | 2006-087478 A | 4/2006 |
| KR | 10-2009-0089528 A | 8/2009 |
| KR | 10-2009-0104261 A | 10/2009 |

(Continued)

*Primary Examiner* — Oren Ginsberg
*Assistant Examiner* — Joshua Lee
(74) *Attorney, Agent, or Firm* — Rabin & Berdo, P.C.

(57) ABSTRACT

A robotic gait training system includes a femoral support unit supporting a thigh of a patient, a hip joint support unit supporting buttocks of the patient, a lower leg support unit supporting a lower leg, an ankle support unit supporting an ankle, a support fixing toe tip positioned at an ankle height of the patient in use, a toe tip pad supporting and wrapping a forefoot of the patient, a tilt sensor, a first linear actuator operation unit rotating the femoral support unit based on the hip joint unit, a second linear actuator operation unit rotating the lower leg supporting unit based on the femoral support unit, a control unit generating a functional electric stimulation (FES) control signal, and an FES unit stimulating the plantarflexor or dorsiflexor of ankle joint based on the FES control signal received from the control unit.

11 Claims, 11 Drawing Sheets

(51) Int. Cl.
*A61H 1/00* (2006.01)
*A61H 1/02* (2006.01)
*A63B 21/00* (2006.01)
*A63B 69/00* (2006.01)
*A61N 1/36* (2006.01)
*A63B 22/02* (2006.01)
*A63B 22/00* (2006.01)

(52) U.S. Cl.
CPC ......... *A63B21/4009* (2015.10); *A63B 21/4011* (2015.10); *A63B 69/0064* (2013.01); *A63B 71/0009* (2013.01); *A61H 1/0262* (2013.01); *A61H 2201/10* (2013.01); *A61H 2201/163* (2013.01); *A61H 2201/1642* (2013.01); *A61H 2201/5069* (2013.01); *A61N 1/36003* (2013.01); *A61N 1/36014* (2013.01); *A63B 22/0235* (2013.01); *A63B 2022/0094* (2013.01); *A63B 2213/004* (2013.01); *A63B 2220/16* (2013.01)

(56) References Cited

U.S. PATENT DOCUMENTS

| | | | |
|---|---|---|---|
| 6,821,233 B1 * | 11/2004 | Colombo et al. | 482/54 |
| 7,429,253 B2 | 9/2008 | Shimada et al. | |
| 2004/0116839 A1 * | 6/2004 | Sarkodie-Gyan | 601/35 |
| 2006/0064047 A1 | 3/2006 | Shimada et al. | |
| 2006/0241539 A1 * | 10/2006 | Agrawal et al. | 602/23 |
| 2008/0255488 A1 * | 10/2008 | Agrawal et al. | 602/23 |
| 2009/0265018 A1 * | 10/2009 | Goldfarb et al. | 623/40 |
| 2011/0066088 A1 | 3/2011 | Little et al. | |
| 2011/0071442 A1 * | 3/2011 | Park et al. | 601/35 |
| 2012/0172770 A1 * | 7/2012 | Almesfer et al. | 601/35 |

FOREIGN PATENT DOCUMENTS

| | | | |
|---|---|---|---|
| KR | 10-2010-0111460 A | 10/2010 | |
| WO | WO 2009/082249 A2 | 7/2009 | |
| WO | WO 2009125397 A2 * | 10/2009 | A61H 1/02 |

* cited by examiner

ACTIVE ROBOTIC GAIT-TRAINING SYSTEM AND METHOD

TECHNICAL FIELD

The present invention relates to an active robotic gait training system and method. In more details, the active robotic gait training system and method can do more active gait training based on remaining gait ability of patients with gait disorder by estimating the gait cycle through the measurement of slope of the lower legs, operating the hip joint and the knee joint by an actuator depending on the gait cycle and operating the ankle joint by functional electric stimulation (FES).

BACKGROUND ART

Gait is one of unique physical features of human beings and it is the most common exercise as well as the basic activity that humans perform every day.

In general, the gait cycle of normal people has the stance phase and the swing phase. Stance phase is the period when the foot is in contact with the ground and it consists of the initial contact step, the foot flat step, the mid stance step, the heel-off step and the toe off step. The swing phase is the period when the foot is off the ground and it consists of the toe off step, the mid swing step and the initial contact step. In normal gait, the stance phase accounts for approximately 60% of the gait cycle and the swing phase accounts for 40% of the gait cycle.

The gait training is a very important unit for patients with gait disorders who lose the gait ability in order to improve the level of independence and the quality of a good life.

Comprehensive assistance of many experts in multiple fields is required for the rehabilitation training to recover the gait ability of patients with gait disorders. In particular, repeated and systematic gait training is required to improve the sense of balance of patients and increase the tolerance of patients.

About 90% of patients with gait disorders are caused by the acquired gait disorders and 50% of acquired disabilities are caused by various diseases. Among them, the stroke accounts for the highest percentage. In the initial period after the occurrence of the stroke, it has been reported that 51% of patients cannot walk at all and 12% of patients can walk with assistance and 37% of patients can walk independently. After the rehabilitation treatment, 64% of patients are recovered to allow them to walk independently, but 36% of patients cannot walk or can walk dependently. Even if the gait function is recovered, abnormal gait patterns may be shown due to the disorders of various motor functions.

In particular, because the extent of possible walking varies depending on patients with gait disorders, the gait training using the patient's own remaining senses could produce a higher effect rather than the uniform gait training.

In order to do this, the accurate judgment on how much patients with gait disorders can currently walk is needed and the gait training based on this judgment is required.

In conventional cases, the gait level of patients with gait disorders was determined by the palpation of a therapist and by using the sensory stimulation.

In the middle of 1980s, the gait training on a treadmill through body weight support was proposed and it was reported that the treatment was clinically effective through this training.

However, the conventional cases had disadvantages in which a couple of therapists held the movement of limbs and trunk of patients with gait disorders and induced the gait while patients with gait disorders performed the training on treadmill.

Also, the passive gait training robot which passively moved the leg joint by the robot joint, was proposed for the elderly and the disabled. However, it was not accurately consistent with the gait path which a patient intended and the fundamental gait pattern for rehabilitation which satisfied the normal gait pattern could not be made.

Therefore, the gait training system is required in which active gait training is available and the joint movement optimal for normal gait pattern is provided by using the remaining senses of patients with gait disorders.

The present invention proposes the active robotic gait training system and method which estimates the gait cycle by measuring the slope of the lower legs, operates the hip joint and knee joint based on the gait cycle by an actuator, operates the ankle joint by functional electric stimulation (FES) and enables more active gait training based on remaining gait ability of patients with gait disorders.

DISCLOSURE

Technical Problem

Accordingly, the present invention is directed to provide an active robotic gait training system and method that it can do more active gait training, by estimating the gait cycle through measurement of slope of the lower leg, operating the hip joint and the knee joint by the actuator depending on the gait cycle and operating the ankle joint by functional electric stimulation.

The present invention is also directed to provide an active robotic gait training system and method which enables patients with gait disorder to perform the active gait training without the aid activities of therapists and provides the joint movement optimal for normal gait pattern.

Technical Solution

In an embodiment according to the present invention, a robotic gait training system is comprised of a femoral support unit, a hip joint support unit, a lower leg support unit, a support fixing toe tip, a tilt sensor, a control unit and a FES unit. The femoral support unit is located on the thigh and has the same length and direction of the thigh. The hip joint support unit is located on the buttocks and one end of the hip joint support is installed on the upper part of the femoral support unit to rotate the femoral support unit. The lower leg support unit is located on the lower leg and is installed on the bottom of the femoral support unit to rotate the lower leg support unit. The support fixing toe tip is located on the lower part of the lower leg support unit and is fixed the strap connecting to the toe tip pad wrapping the toe tip (forefoot). The tilt sensor is installed on the lower part of lower leg support unit or on one side of the toe tip pad. The control unit generates FES control signal to do functional electric stimulation (FES) to plantarflexor or dorsiflexor of ankle joint by using the slope signal received from the tilt sensor. The FES unit is formed to do FES to plantarflexor or dorsiflexor of ankle joint based on FES control signal received from the control unit.

In another embodiment according to the present invention, a robotic gait training system is comprised of the femoral support unit, the hip joint support unit, the lower leg support unit, the support fixing toe tip, the tilt sensor, a control unit and a first linear actuator operation unit. The control unit generates the hip joint angle control signal by using the slope signal received from the tilt sensor. The first linear actuator operation unit receives the hip joint angle control signal from the control unit and operates the first linear actuator to rotate the femoral support unit based on the hip joint angle control signal in the hip joint unit that is the coupling unit between the femoral support unit and the hip joint support unit.

In another embodiment according to the present invention, a robotic gait training system is comprised of the femoral support unit, the hip joint support unit, the lower leg support unit, the support fixing toe tip, the tilt sensor, a control unit and a second linear actuator operation unit. The control unit generates the knee joint angle control signal by using the slope signal received from the tilt sensor. The second linear actuator operation unit receives the knee joint angle control signal from the control unit and operates the second linear actuator to rotate the lower leg support unit based on the knee joint angle control signal in the knee joint unit that is the coupling unit between the lower leg support unit and the femoral support unit.

The control unit estimates the gait cycle from the slope signal and generates the hip joint angle control signal based on the estimated gait cycle by using previously stored hip joint operation pattern, and the control unit estimates the gait cycle from the slope signal and generates the knee joint angle control signal based on the estimated gait cycle by using previously stored knee joint operation pattern.

One side of the first linear actuator is installed on one end of the hip joint support unit and the other side of the first linear actuator is installed on the upper part of femoral support unit and one side of the second linear actuator is installed on one end of the femoral support unit and the other side of the second linear actuator is installed on the upper part of the lower leg support unit.

The hip joint unit is equipped with the first encoder to measure the rotated angle of the femoral support unit and the knee joint unit is equipped with the second encoder to measure the rotated angle of the lower leg support unit.

The control unit estimates the gait cycle from the slope signal and receives the hip joint angle signal from the first encoder, and then generates the hip joint angle control signal based on the estimated gait cycle by using the previously stored hip joint operation pattern. Also, the control unit estimates the gait cycle from the slope signal and receives the knee joint angle signal from the second encoder, and then generates the knee joint angle control signal based on the estimated gait cycle by using the previously stored knee joint operation pattern.

The first load cell is installed between the first linear actuator and the femoral support unit and the second load cell is installed between the second linear actuator and the lower leg support unit.

The femoral support unit, the hip joint support unit and the lower leg support unit form the robot-assisted gait training device for one side leg and the robotic gait training system contains one pair of robot-assisted gait training device for left and right sides of legs and contains the treadmill that a person who put on one pair of the robot-assisted gait training device does the gait training.

The robotic gait training system contains the harness, the frame to install the pulley that the rope installed on the harness goes through, and the counterweight installed on one end of the rope passing through the pulley.

The femoral strap to couple the femoral support unit and the thigh is installed on the femoral support unit and it contains the lower leg strap to couple the upper part of lower leg support unit and the lower leg and contains the ankle strap to couple the lower part of lower leg support unit and the ankle.

In another embodiment according to the present invention, a operation method of the robotic gait training system is comprised of: the step collecting the gait pattern, which collects the gait pattern of patients with gait disorders and analyzes the motions; the step making database by patients with gait disorders, which stores the collected gait pattern and the results of analysis from the step collecting the gait pattern; the system control step, which generates FES control signal and generates the signal to control the actuator operating the hip joint unit and the knee joint unit, using the gait pattern stored from the step making database by patients with gait disorders. The step collecting the gait pattern is further comprising: the step collecting the gait pattern by patients, which measures the gait of patients with gait disorders and collects the gait pattern; the step detecting the gait parameters, which detects the joint angle, the gait cycle, the gait speed and the gait event including gait timing; the step producing the gait pattern of the training, which generates the gait pattern for gait training, by using the gait parameters detected at the step detecting the gait parameters.

The step making database by patients with gait disorders has further comprising: the step setting the initial gait pattern, which reads the initial gait pattern selected among the previously stored gait patterns; the step generating the personal adaptive training pattern, which re-adjusts the gait pattern for training by using the initial gait pattern read in the step setting the initial gait pattern, the gait pattern for training generated in the step producing the gait pattern of the training and the previously stored database of patients with gait disorders; and the step updating the database, which stores and updates the information of the gait pattern re-adjusted in the step generating the personal adaptive training pattern.

The system control step has further comprising: the step setting the FES sensor, which sets the stimulation speed and the stimulation location of the FES sensor depending on the intensity level of the training set; the gait training simulation step, which determines whether it is normal by examining the situation of the system operation when the gait training simulation is carried out with the gait training pattern, when the patient are not getting on the robotic gait training system.

Advantageous Effects

According to the active robotic gait training system and method of the present invention, it can do the training customized to the patient's own pace, by estimating the gait cycle through measurement of slope of the lower leg, operating the hip joint and the knee joint by the actuator depending on the gait cycle and operating the ankle joint by functional electric stimulation (FES).

Thus, the gait training can be made according to the patient's own willingness, and more active gait training is available.

In addition, the present invention enables the active gait training of patients with gait disorders without the support activities of the therapists and the active robotic gait training providing the joint training optimal for normal gait pattern.

BEST MODE

Hereinafter, preferred embodiments of the present invention will be described below in more detail with reference to the accompanying drawings.

Figure 1:
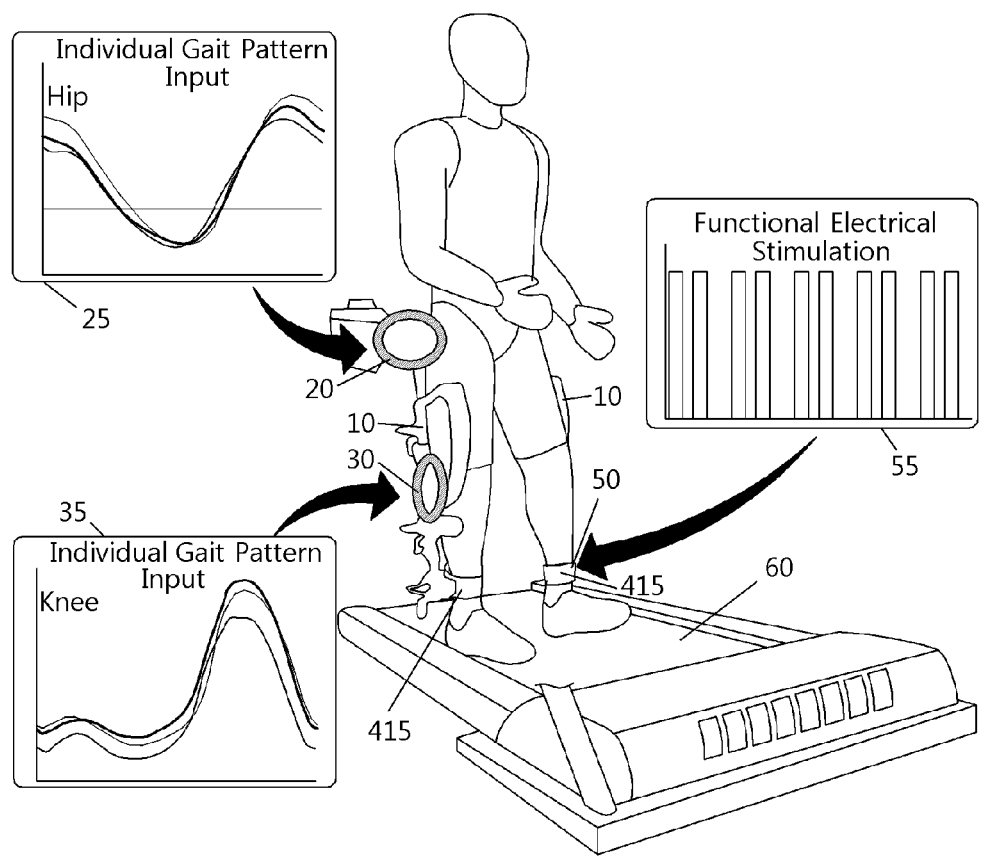
FIG. 1 is a schematic diagram to briefly describe active robotic gait training system of the present invention.

FIG. 1 is a schematic diagram to explain the overview of the active robotic gait training system of the present invention.

A trainee who is a patient of gait disorder wears the robot-assisted gait training device (10) on both legs and takes the training on the treadmill (60).

Robot-assisted gait training device (10) includes the hip joint unit (20), the knee joint unit (30), the ankle strap (415), the FES unit (50) and the tilt sensor (not shown).

The tilt sensor (not shown) detects the slope of lower leg region (or foot) once it is installed on robot-assisted gait training device (10).

The hip joint unit (20) is made to rotate the hip joint at a predetermined angle by operation of actuator (motor) and it is operated by receiving the signal to operate the hip joint actuator based on hip joint operation pattern (25) during the gait cycle previously set, from the control unit (not shown).

The knee joint unit (30) is made to rotate the knee joint at a predetermined angle by operation of actuator (motor) and it is operated by receiving the signal to operate the knee joint actuator based on knee joint operation pattern (35) during the gait cycle previously set, from the control unit (not shown).

The ankle strap (415) is one of means to install robot-assisted gait training device (10) on the leg and the bottom of robot-assisted gait training device (10) is fixed and installed on the ankle.

The FES unit (50) is one of means for applying the functional electric stimulation (FES) to the plantarflexor or dorsiflexor of ankle joint and it is operated by receiving the electrical stimulation signal based on the predetermined function electrical stimulation pattern (55) from the control unit (not shown). The predetermined functional electric stimulation pattern (55) may be made of the pulse train. The FES unit (50) can be placed on the part of the ankle or instep.

The FES unit (50) is operated at the time of pre-swing (toe off) on the ROM (range of motion) curve. The time of pre-swing (toe off) can be the point of 60% when the entire of 1 gait cycle is referred to as 100%. Namely, the pre-swing (toe off) can be the point that changes from the stance period to the swing period.

The control unit (not shown) determines current gait cycle based on the signal received from the tilt sensor (not shown) and operates hip joint unit (20), knee joint unit (30) and FES unit (50) based on determined gait cycle. The hip joint unit (20) is operated based on hip joint operating pattern (25) during predetermined gait cycle and the knee joint unit (30) is operated based on knee joint operating pattern (35) during predetermined gait cycle. FES unit (50) stimulates the muscle related to the ankle joint based on predetermined functional electric stimulation pattern (55).

In other words, the robot-assisted gait training device (10) controls the passive gait training of hip joint and knee joint of patients with gait disorders like patients with spinal cord injury or stroke, based on the characteristics of normal gait by using a linear actuator driven by a servo motor. It can induce the active gait training by applying functional electric stimulation (FES) to the plantarflexor/dorsiflexor of ankle joint based on gait cycle of the paralyzed patients detected by a tilt sensor. Hip joint operation pattern (25) shows the operation of an actuator operating the hip joint based on the characteristics of normal gait of patients with gait disorders. Knee joint operation pattern (35) shows the operation of an actuator operating the knee joint based on the characteristics of normal gait of patients with gait disorders. Predetermined functional electric stimulation pattern (55) shows the action which induces active gait training by applying functional electric stimulation (FES) to the plantarflexor/dorsiflexor of ankle joint based on characteristics of normal gait of patients with gait disorders.

Figure 2:
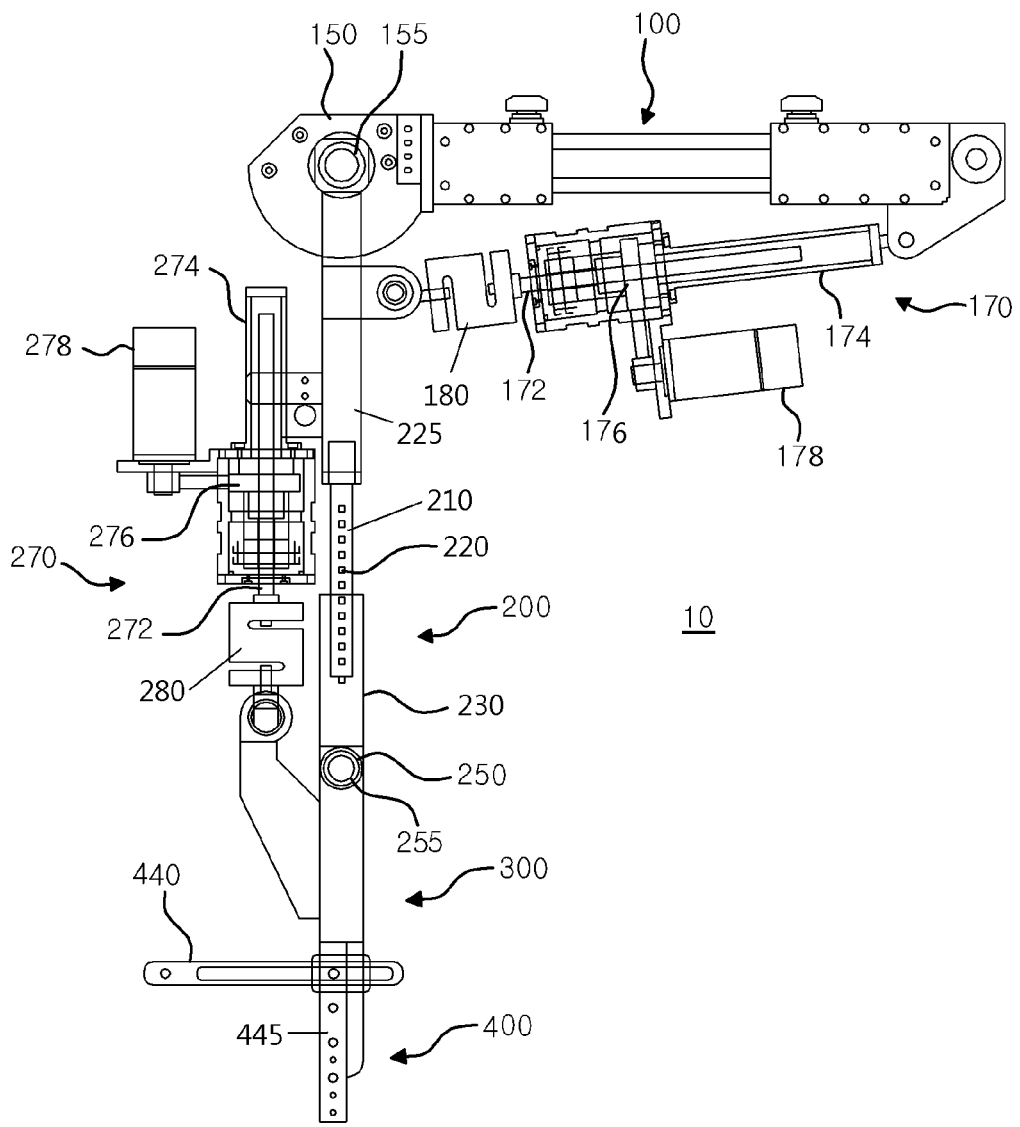
FIG. 2 is a block diagram to describe the configuration of robot-assisted gait training device created by the present invention.
Figure 3:
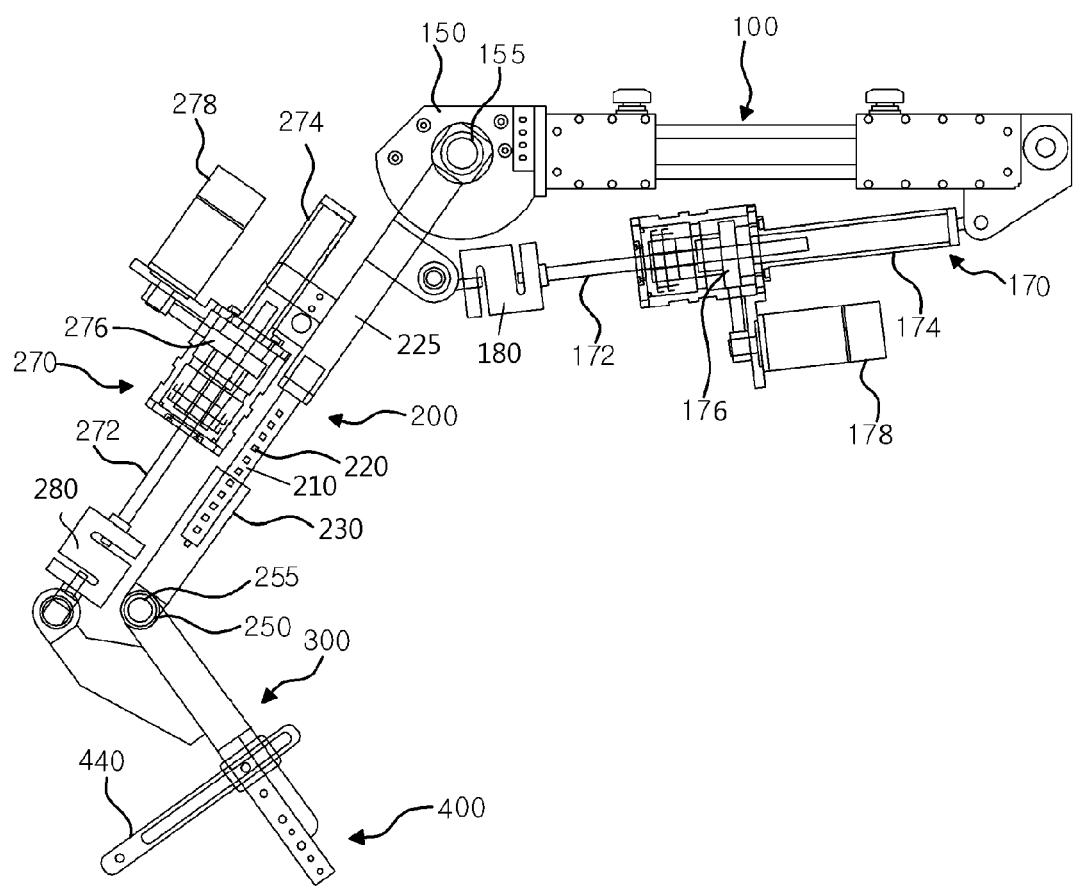
FIG. 3 is an example of the operating form of robot-assisted gait training device in FIG. 2.

FIG. 2 is a block diagram that describes the configuration of robot-assisted gait training device in the present invention. FIG. 3 is an example of the operating form of robot-assisted gait training device in FIG. 2.

The robot-assisted gait training device (10) consists of the hip support unit (100), the femoral support unit (200), the lower leg support unit (300), ankle support unit (400), hip joint unit (150) and knee joint unit (250).

The hip joint support unit (100) is installed on hip areas of the left and right sides of the body which is the buttock, and holds the femoral support unit (200) installed on hip joint unit (150) in order to be rotated by the first linear actuator (170). The hip joint unit (150) is installed on one end of hip joint support unit (100).

The hip joint unit (150) is installed between the hip support unit (100) and the femoral support unit (200). The hip joint support unit (150) is fixed and installed on the hip joint unit (150). The femoral support unit (200) is installed to be rotated on the hip joint unit (150). In other words, the hip joint unit (150) acts as a joint which enables hip joint support unit (100) and femoral support unit (200) to be rotated. The first rotation angle encoder (155) which measures the joint rotation angle can be installed on hip joint unit (150). The first rotation angle encoder (155) generates the signal to identify the gait characteristics by repeatedly measuring the joint rotation angle of patients with gait disorders. The control signal which operates hip joint unit (150) based on gait characteristics of patients with gait disorders can be generated by using this signal.

The first linear actuator (170) includes the piston (172), cylinder (174), gear unit (176) and servo motor (178) and it is the actuator making a linear motion. One side of the first linear actuator (170) is installed on one end of hip joint support unit (100) and the other side is installed on the upper part of femoral support unit (200) through the first load cell (180). The first load cell (180) can be omitted in a certain case.

Piston (172) is the threaded piston. One end of piston (172) is fixed on the femoral support unit (200) through the first load cell (180) and the other end is accommodated within the cylinder (174) fixed on the hip joint support unit (100).

The cylinder (174) accommodates piston (172) and one end is fixed on the hip joint support unit (100). The other end is fixed on the femoral support unit (200) through the first load cell (180) connected to the piston (172) accommodated in the cylinder (174).

The gear unit (176) is penetrated and coupled to be rotated on the threads of the piston (172).

Piston (172), cylinder (174) and gear unit (176) can be referred to as ball screw and ball screw is the means to change the rotation of the servo motor (178) into the linear motion.

The servo motor (178) makes the piston (172) move as the round exercise to the in/outside of cylinder (174) by rotating the gear unit (176).

The first load cell (180) measures the force (load) applied to lift the femoral support unit (200) in hip joint unit (150). In other words, it measures the force applied on the hip joint by the first linear actuator (170).

The femoral support unit (200) is installed on the location of the femoral region in the left and right sides of body. One end of the femoral support unit (200) is installed to rotate on the hip joint unit (150) and the other end is fixed on the knee joint unit (250). The femoral support unit (200) is rotated by the first linear actuator (170) and the actions to lift up and down the femoral region are made. Also, the femoral support unit (200) gives the support to rotate the lower leg support unit (300) by the second linear actuator (270) and the lower leg support unit (300) installed the knee joint unit (250). The femoral support unit (200) is fixed on the femoral region of body by the strap.

Since the femoral support unit (200) supports the femoral region and the length of the thigh may vary depending on people, the femoral extension unit (210) located between upper femoral support unit (225) and lower femoral support unit which the femoral support unit (200) is divided into is further provided.

The femoral extension unit (210) is the bar shape in which one end of the femoral extension unit (210) is fixed on the upper femoral support unit (225) and it comprises a plurality of holes (220). The other end of the femoral extension unit (210) is inserted into the lower femoral support unit (230), and hole of the outside of lower femoral support unit (230) is coupled to the screw with holes (220) of the other end of the femoral extension unit (210). The length can be changed by the femoral extension unit (210).

The knee joint unit (250) is installed between the femoral support unit (200) and lower leg support unit (300). The femoral support unit (200) is fixed and installed on the knee joint unit (250) and the lower leg support unit (300) is installed to be rotated on the knee joint unit (250).

In the knee joint unit (250), the second rotation angle encoder (250) which measures the joint rotation angle can be installed. The second rotation angle encoder (250) generates the signal to identify the gait characteristics by repeatedly measuring the joint rotation angle of patients with gait disorders. The control signal operating the knee joint unit (250) based on the gait characteristics of patients with gait disorders can be generated by using this signal (output signal of the second rotation angle encoder (250)).

The second linear actuator (270) includes the piston (272), cylinder (274), gear unit (276) and servo motor (278) and it is the actuator making a linear motion. One side of the second linear actuator (270) is installed on the femoral support unit (200) and the other side is installed on the upper side of lower leg support unit (300) through the second load cell (280). The second load cell (280) can be omitted.

Piston (272) is the threaded piston. One end of piston (272) is fixed on the lower leg support unit (300) through the second load cell (280) and the other end of piston (272) is accommodated within the cylinder (274) fixed on the femoral support unit (200).

The cylinder (274) accommodates the piston (272) and one end of the cylinder (274) is fixed on the femoral support unit (200). The other end of the cylinder (274) is fixed on the lower leg support unit (300) through the second load cell (280) connected to the piston (272) accommodated in the cylinder (274).

The gear unit (276) is penetrated and coupled to be rotated on the threads of the piston (272).

Piston (272), cylinder (274) and gear unit (276) can be referred to as ball screw and ball screw is the means to change the rotation of the servo motor (278) into the linear motion.

The servo motor (278) makes the piston (272) move as the round exercise to the in/outside of cylinder (274) by rotating the gear unit (276).

The second load cell (280) measures the force (load) applied to lift the lower leg support unit (300) in hip joint unit (150). In other words, the second load cell (280) measures the force applied by the second linear actuator (270).

The lower leg support unit (300) is installed on the location of the lower leg region in the left and right sides of body. One end of the lower leg support unit (300) is installed to rotate on the knee joint unit (250) and the other end of the lower leg support unit (300) is connected to the ankle support unit (400). The lower leg support unit (300) is rotated by the second linear actuator (270) and the actions to lift up and down the legs are made. The lower leg support unit (300) corresponds to the calf of body and it is fixed with the lower leg support unit (300) and the calf by a strap.

One end of the ankle support unit (400) is connected to the lower leg support unit (300) and the support fixing toe tip (440) is installed on the one end of the ankle support unit (400). The ankle support unit (400) is equipped with an ankle strap and the ankle support unit (400) can be fixed to the ankle.

The strap connecting to the toe tip pad (forefoot strap) (441) wrapping the toe tip (forefoot) fixes to the hole of the support fixing toe tip (440) and the toe tip (forefoot) part is fixed.

FES stimulation part (not shown) can be installed on the foot through the support fixing toe tip (440).

The ankle extension unit (445) is the bar shape in which one end of the ankle extension unit (445) is fixed on the ankle support unit (400) and it comprises a plurality of holes (220). The hole of the outside of ankle support unit (400) is coupled to the screw, and the length of ankle support unit (400) can be changed. The ankle extension unit (445) can be omitted in a certain case.

Figure 4:
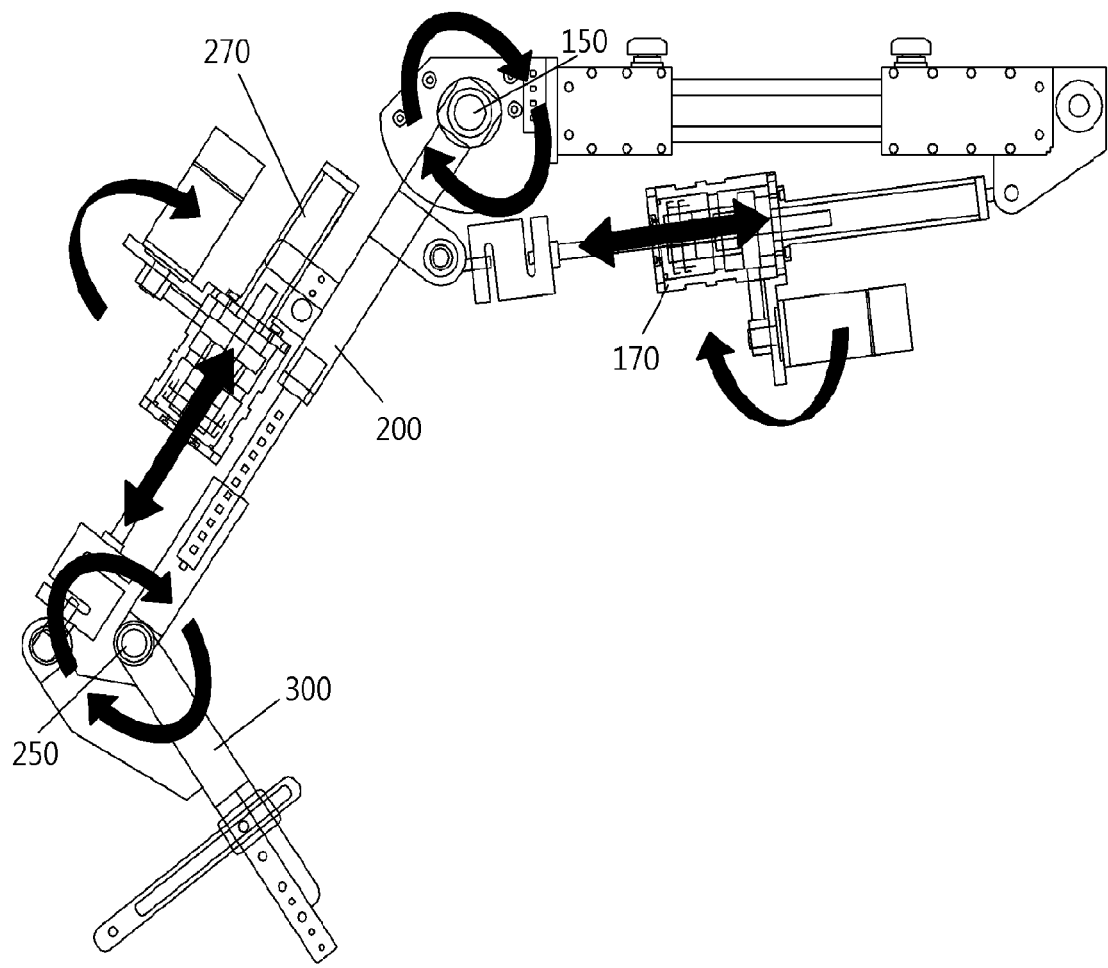
FIG. 4 is a diagram showing the operating principle of a robot-assisted gait training device that is operated.

FIG. 4 is a diagram showing the operating principle of a robot-assisted gait training device that is operated.

If the first linear actuator (170) moves towards the hip joint unit (150) or the first load cell (180), the hip joint unit (150) moves clockwise and the femoral support unit (200) moves upward. In other words, the femoral support unit (200) moves in the direction of lifting up the thigh. If the first linear actuator (170) moves in the opposite direction, as the result, the femoral support unit (200) moves downward. In other words, the femoral support unit (200) moves in the direction of lifting down the thigh.

If the second linear actuator (270) moves towards the hip joint unit (150), the knee joint unit (250) moves clockwise, and the lower leg support unit (300) moves upward. In other words, the lower leg support unit (300) moves in the direction of lifting up the lower leg (calf). If the second linear actuator (270) moves towards the ankle unit (400), as the result, the lower leg support unit (300) moves downward. In other words, the lower leg support unit (300) moves in the direction of lifting down the lower leg.

Figure 5:
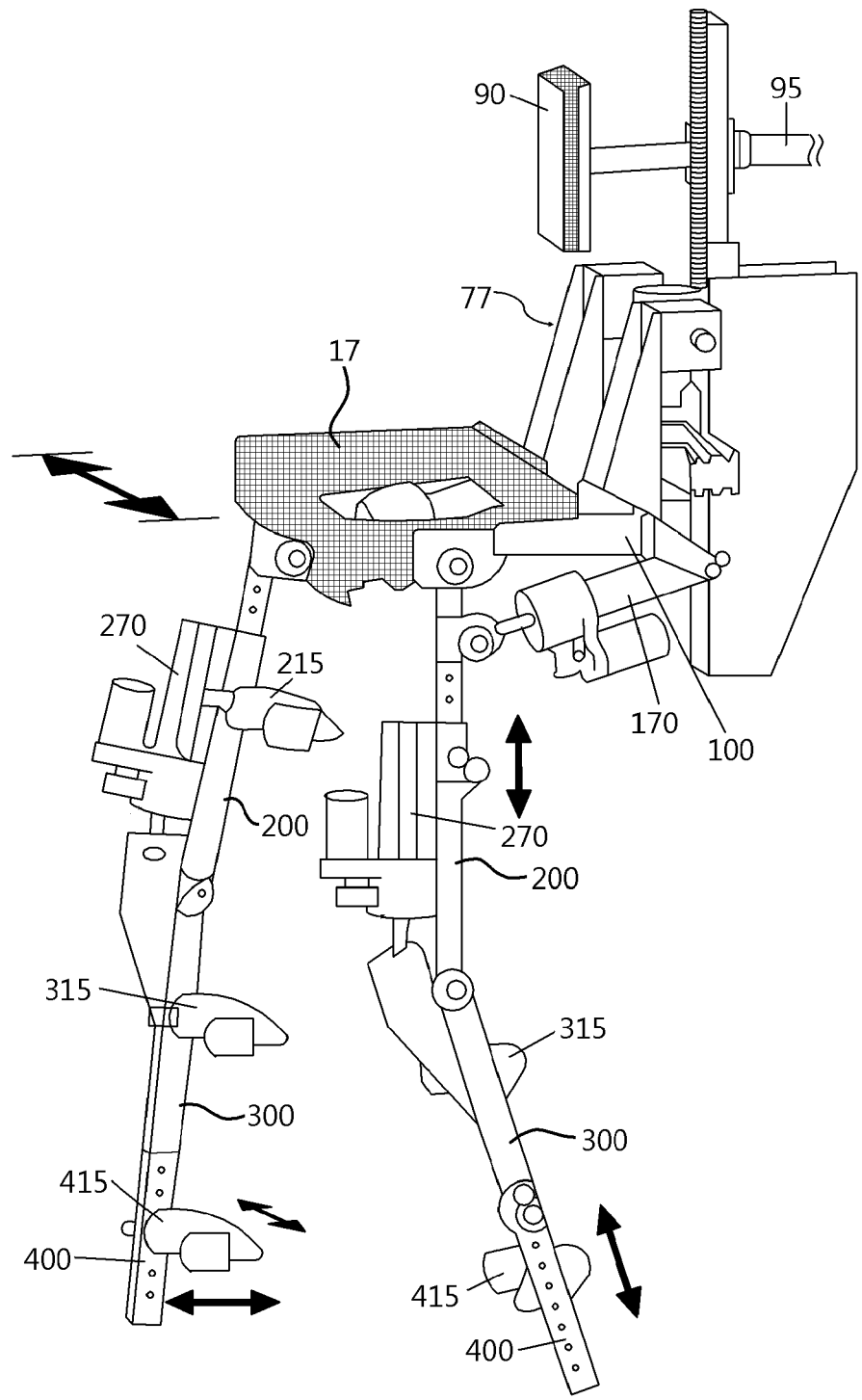
FIG. 5 is an explanation drawing to describe the robotic gait training system in which combines the robot-assisted gait training device of left leg and the robot-assisted gait training device of right leg.

FIG. 5 is an explanation drawing to describe the robotic gait training system in which have with robot-assisted gait training device of left leg and robot-assisted gait training device of right leg.

In the robot-assisted gait training device (10) of the left and right legs, one end (it is opposite to the hip joint unit (150)) of the hip joint support unit (100) is installed and fixed on the integrated fixation end (77). The back support unit (90) is installed on one side of the integrated fixation end (77) to support the back when wearing this robotic gait training system. In addition, the integrated fixation end (77) is connected to the frame of robotic gait training system through the frame joint unit (95). The frame is a frame to install the harness.

The robot-assisted gait training device (10) of left and right sides of legs is equipped with the femoral strap (215), lower leg strap (315) and ankle strap (415), and these combine the leg with the robot-assisted gait training device (10).

The buttock guide (17) is located on the upper side of robot-assisted gait training device (10) and is positioned on both right side and left side of the hip. The buttock guide (17) plays a role as a cushion to mitigate the pain caused by pressing the skin by robot-assisted gait training device (10).

In other words, the hybrid robot-assisted gait training device in the present invention is a gait training device that reinforces the muscular strength so as to make the patient with gait disorders move the joints of the legs and does the gait training. It includes the hip joint support unit (100), the femoral support unit (200) and the lower leg support unit (300) connecting to the waist & hip area, the thigh and calf of the human body, respectively. It also includes the hip joint unit (150) and the knee joint unit (250) coupled to rotate each support unit. Hip support unit (100) corresponding to the waist and hip areas of the human body can be simply responsible for bearing the weight of the femoral support unit (200) and the lower leg support unit (300). Also, hip support unit (100) can bear the weight of the upper body by coupling the upper body and it by a strap. The femoral support unit (200) fixes the femur (thigh) by coupling by a strap on the thigh of the human body. The lower leg support unit (300) corresponding to the calf of human body can be fixed with human body by coupling the calf and it with a strap.

Figure 6:
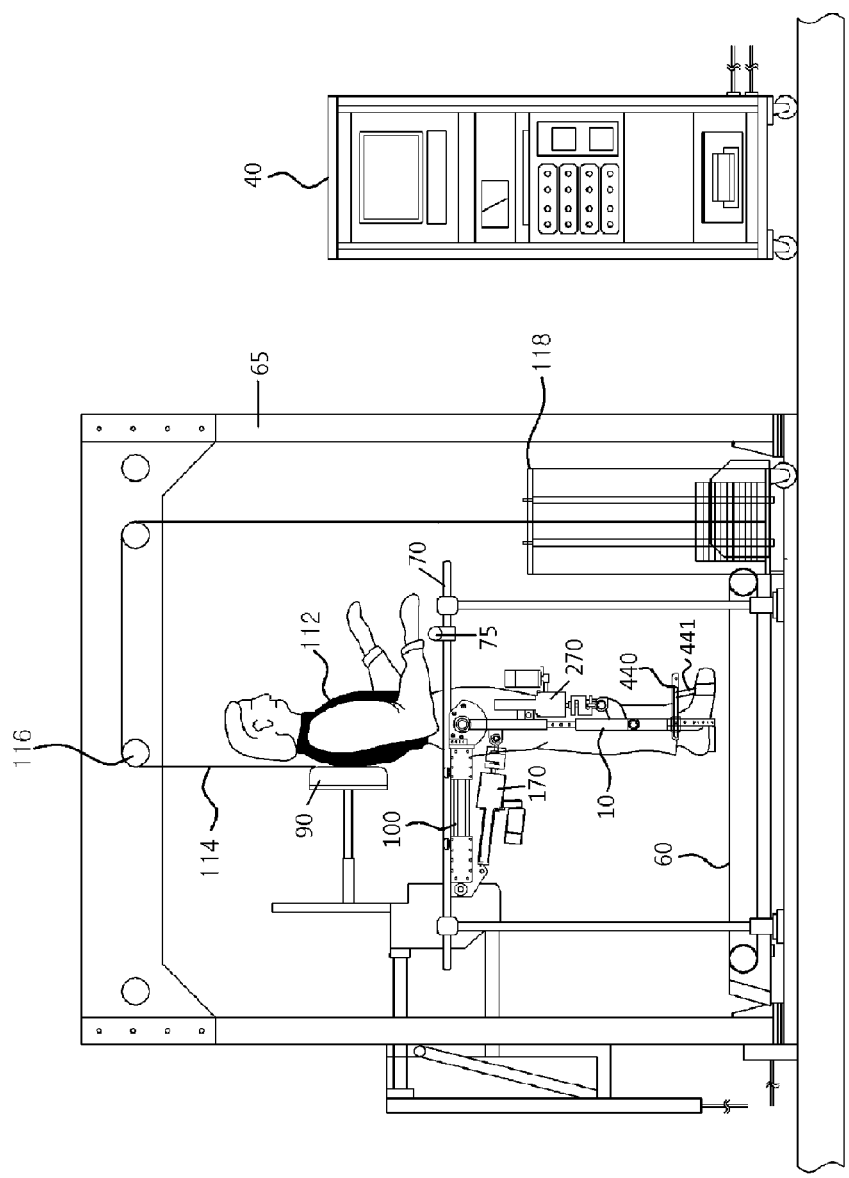
FIG. 6 is an explanation drawing to describe the state of use of the active robotic gait training system of the present invention.

FIG. 6 is an explanation drawing to describe the state of use of the active robotic gait training system of the present invention.

Once patients with gait disorders are equipped with harness (112) and the robot-assisted gait training device (10) on the left and right sides of legs, they are taking the gait training on the treadmill (60).

A rope (114) installed on the harness (112) to support the weight of patients with gait disorders is installed on the frame (65). It is connected to the counterweight (118) to support the weight through a pulley (116) installed on the upper side of patients with gait disorders. In other words, it consists of the harness (112), the pulley (116) and the counterweight (118), to bear the weight of patients with gait disorders. A pulley (116) supports the weight of patient with gait disorders through a rope (114) connected to the harness (112) which the patient wears. A counterweight (118) controls the vertical movement of patients with gait disorders through the rope (114).

The arm holder (70) which patients with gait disorders can hold with hands during the gait training is located on the left and right sides. Since the stop switch (75) is equipped on the arm holder (70), the training can be stopped by a trainee during the training upon the occurrence of emergency.

The control unit (40) determines the status and gait cycle of pedestrian from the signal received from a tilt sensor and a load cell. It operates the hip joint unit (20), the knee joint unit (30) and FES unit (50) according to the determined gait cycle.

Also, the patients with gait disorders can take the gait training while they are looking at the display of results of training on the display unit of the control unit (40), and the effect of biofeedback is brought.

Figure 7:
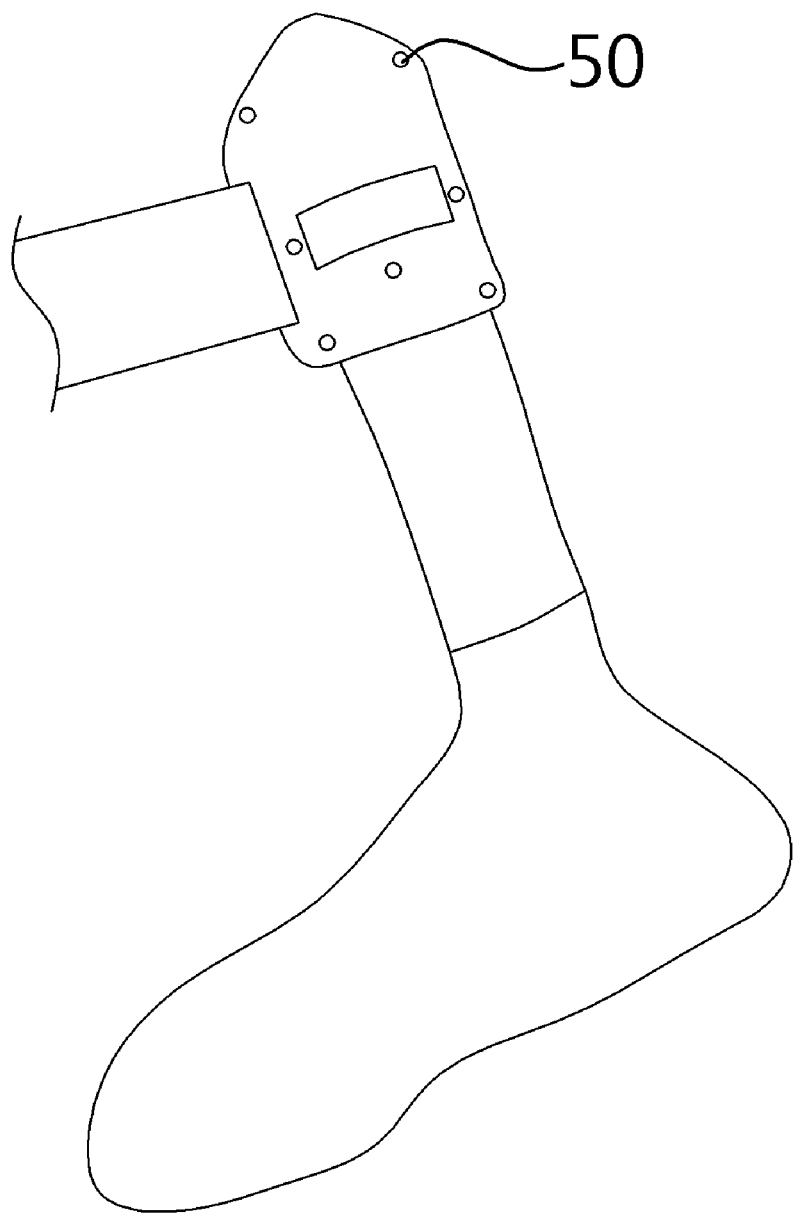
FIG. 7 is an example of FES unit integrated with a strap.
Figure 8:
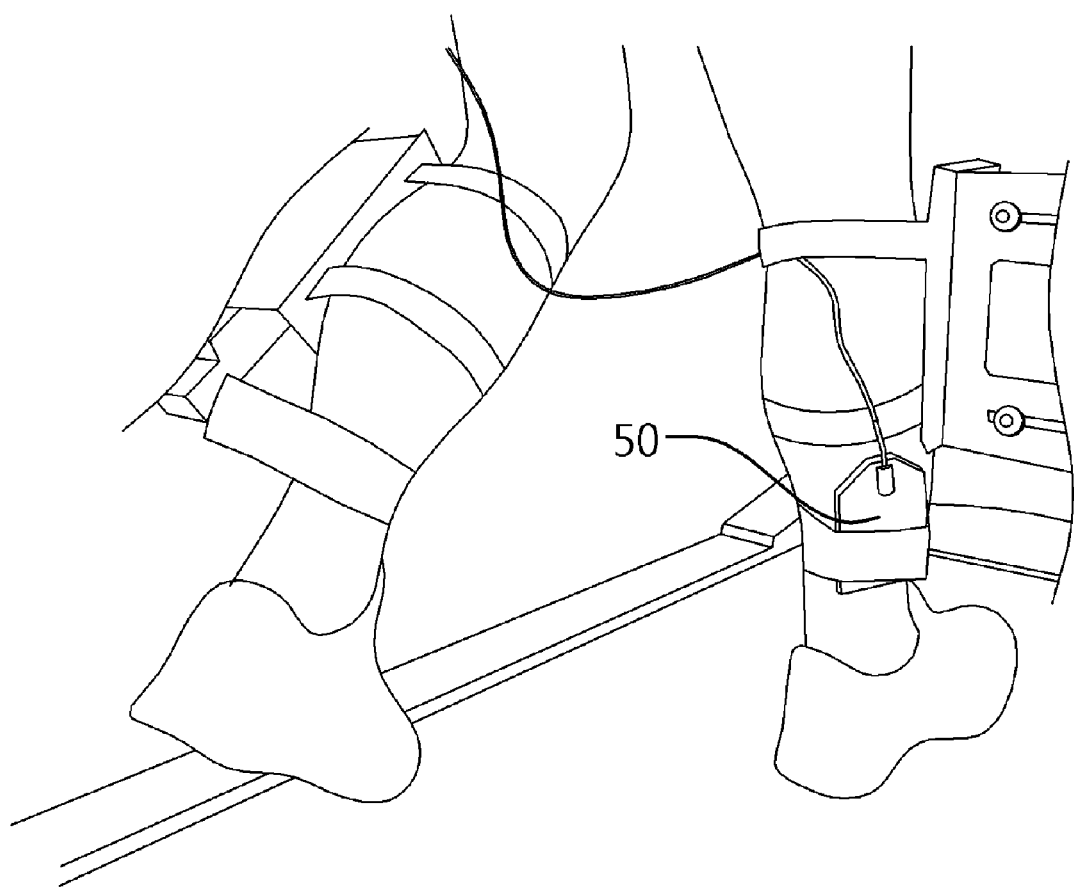
FIG. 8 shows an example of the FES unit installed using a strap in the present invention.

FIG. 7 is an example of FES unit integrated with a strap in the present invention. FIG. 8 shows an example of the FES unit installed using a strap in the present invention.

FES unit (50) is located at the bottom of the lower leg support unit (300) and applies a functional electric stimulation (FES) to the ankle part of the human body by the control unit (40).

The electric stimulation unit (50) can take shape of a strap or a sock, and apply FES (Functional Electric Stimulation) stimulus to the ankle part of the human body by contacting the strap or the sock.

The gait training device (10) is equipped with the first rotational angle encoder (155) which measures the joint rotational angle on the hip joint unit (150), and the second rotational angle encoder (250) which measures the joint rotational angle on the knee joint unit (250) in the present invention. The joint rotational angle detected in the rotational angle encoders (155, 255) is sent to the control unit (40). The control unit (40) makes the database of the gait characteristics of each patient with gait disorders by using the repetitive rotational angle data, and controls the amount and speed of rotation of the servo motors (178, 278) based on the each gait characteristic, and as the results, controls the linear actuator (170, 270).

In addition, the gait training device (10) has the load cell measuring the load applied to the hip joint unit (150) and the load cell measuring the load applied to the knee joint unit (250), in the present invention. The load cell transmits the weight applied to the joint unit (150, 250) to the control unit. The control unit (40) controls the counterweight (118) so as to take the appropriate tension, depending on the gait characteristics of patients with gait disorders. Thus, it controls the tension applied to the harness (112) coupled to the rope (114) and the pulley (116), and each patient with gait disorders can do the optimized gait training according to personal gait characteristics.

In addition, the second support unit (25) is equipped with the tilt sensor to measure the slope with reference to earth axis and the electric stimulation unit (40) applies the functional electric stimulation to the plantarflexor/the dorsiflexor of ankle joint for each gait cycle of the patients with gait disorders measured by the tilt sensor, and then the patients can do active gait training. Electrical stimulation unit (40) can detect the moment of the gait measured by the tilt sensor and produce the functional electric stimulation. It also can produce the functional electric stimulation for each gait cycle in accordance with the gait training optimized from the database for the gait characteristics of each patient with gait disorders accumulated in the control unit (40).

Figure 9:
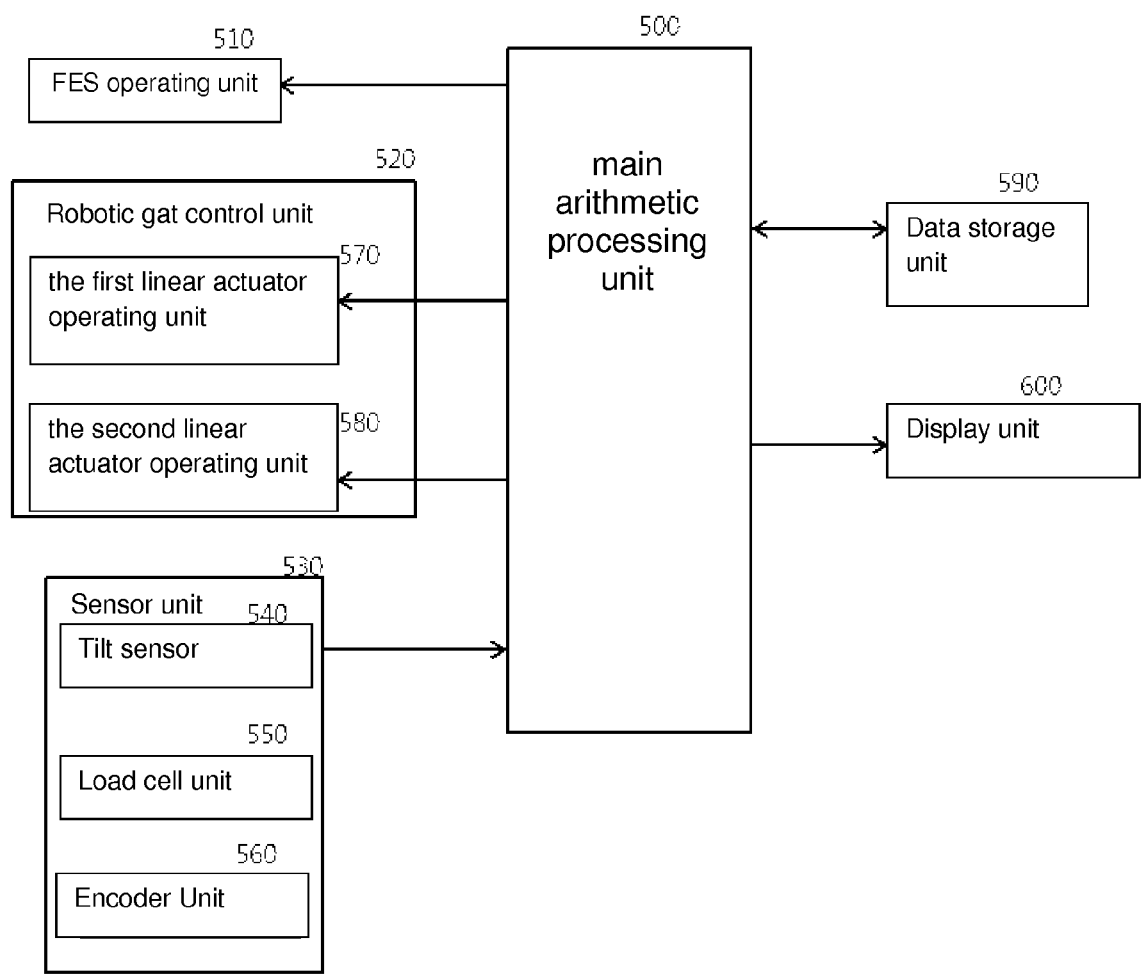
FIG. 9 is a block diagram for an overview of the configuration to control the active robotic gait training system of the present invention.

FIG. 9 is a block diagram for an overview of the configuration to control the active robotic gait training system of the present invention. It includes the main arithmetic processing unit (500), the FES operating unit (510), the robotic gait control unit (520), the sensor unit (530), the data storage unit (590) and the display unit (600).

The main arithmetic processing unit (500) receives the output signal of the sensor unit (530) and receives the gait cycle pattern previously stored from the data storage unit (590). It generates the FES control signal, the first linear actuator control signal and the second linear actuator control signal. It sends the signal to the FES operation unit (510), the first linear actuator operation unit (570) and the second linear actuator operation unit (580) of robotic gait control unit (520). Also, the output signal received from the sensor unit (530) is stored in the data storage unit (590). The main arithmetic processing unit (500) analyzes the result of gait training of patients with gait disorders and shows the output on the display unit (600).

The FES operation unit (510) gives the output of FES stimulation signal according to FES control signal of the main arithmetic processing unit (500).

The robotic gait control unit (520) includes the first linear actuator operation unit (570) and the second linear actuator operation unit (580).

The first linear actuator operation unit (570) operates the first linear actuator (170) by the first linear actuator control signal received from the main arithmetic processing unit (500). The first linear actuator (170) is rotated to lift up or down the femoral support unit (200).

The second linear actuator operation unit (580) operates the second linear actuator (270) by the second linear actuator control signal received from the main arithmetic processing unit (500). The second linear actuator (270) is rotated to lift up or down the lower leg support unit (300).

The sensor unit (530) includes a tilt sensor (540), a load cell unit (550) and the encoder unit (560), and it sends the detected signal to the main arithmetic processing unit (500).

The tilt sensor (540) is installed on the lower leg support unit of the robot-assisted gait training device (10) and on the toe tip pad wrapping the forefoot (toe tip).

The load cell unit (550) includes the first load cell (180) and the second load cell (280). The first load cell (180) measures the force (load) applied to the hip joint unit (150) in order to lift up the femoral support unit (200). The second load cell (280) measures the force (load) applied to the knee joint unit (250) in order to lift up the lower leg support unit (300).

The encoder (560) includes the first rotation angle encoder (155) and the second rotation angle encoder (255). The first rotation angle encoder (155) measures the rotation angle of the hip joint and the main arithmetic processing unit (500) generates the first linear actuator control signal by using it. The second rotation angle encoder (255) measures the rotation angle of the knee joint and the main arithmetic processing unit (500) generates the second linear actuator control signal by using it. In other words, the main arithmetic processing unit (500) produces the signal to identify the gait characteristics by repeatedly measuring the joint rotation angle of patients with gait disorders through the encoder unit (560). Then, the main arithmetic processing unit (500) process the signal, and produces the control signal which operates the hip joint unit (150) and the knee joint unit (250) based on the gait characteristics of patient with gait disorders.

The data storage unit (590) stores the signal received from the main arithmetic processing unit (500), and the display unit (600) displays the signal received from the main arithmetic processing unit (500).

Figure 10:
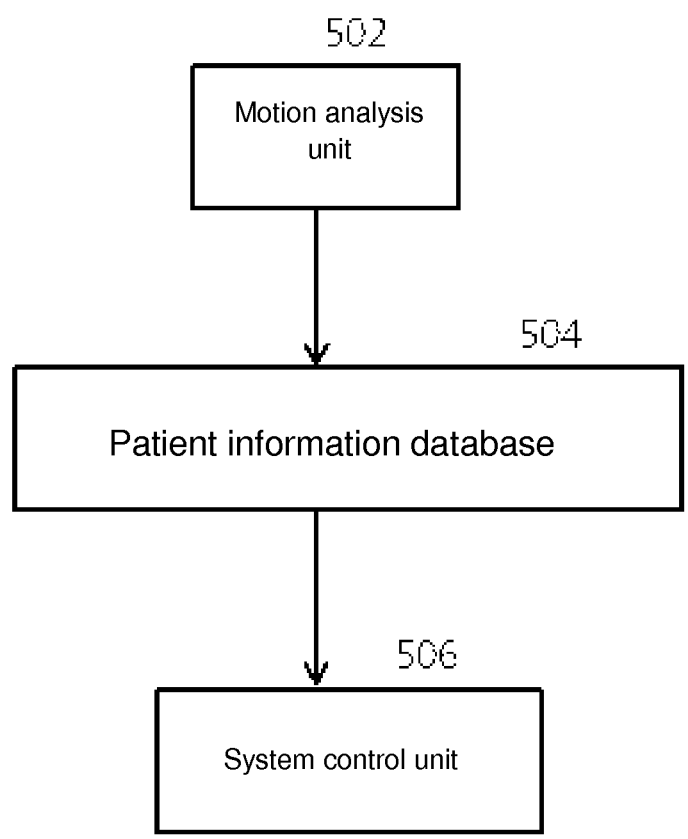
FIG. 10 is a block diagram for an overview of the configuration of the main arithmetic processing unit of FIG. 9.

FIG. 10 is a block diagram for an overview of the configuration of the main arithmetic processing unit of FIG. 9, and it includes the motion analysis unit (502), the patient information database (504) and the system control unit (506).

The motion analysis unit (502) collects the gait pattern of patients, especially patients with gait disorders and analyzes the motions.

Patient information database (504) stores the gait patterns and the analysis results received from the motion analysis unit (502) by patients.

The system control unit (506) reads the gait patterns from the patient information database (504), generates the FES control signals, the first linear actuator control signal and the second linear actuator control signal, and then transmits them to the FES operation unit (510), the first linear actuator operation unit (570) of the robotic gait control unit (520) and the second linear actuator operation unit (580) of the robotic gait control unit (520).

Figure 11:
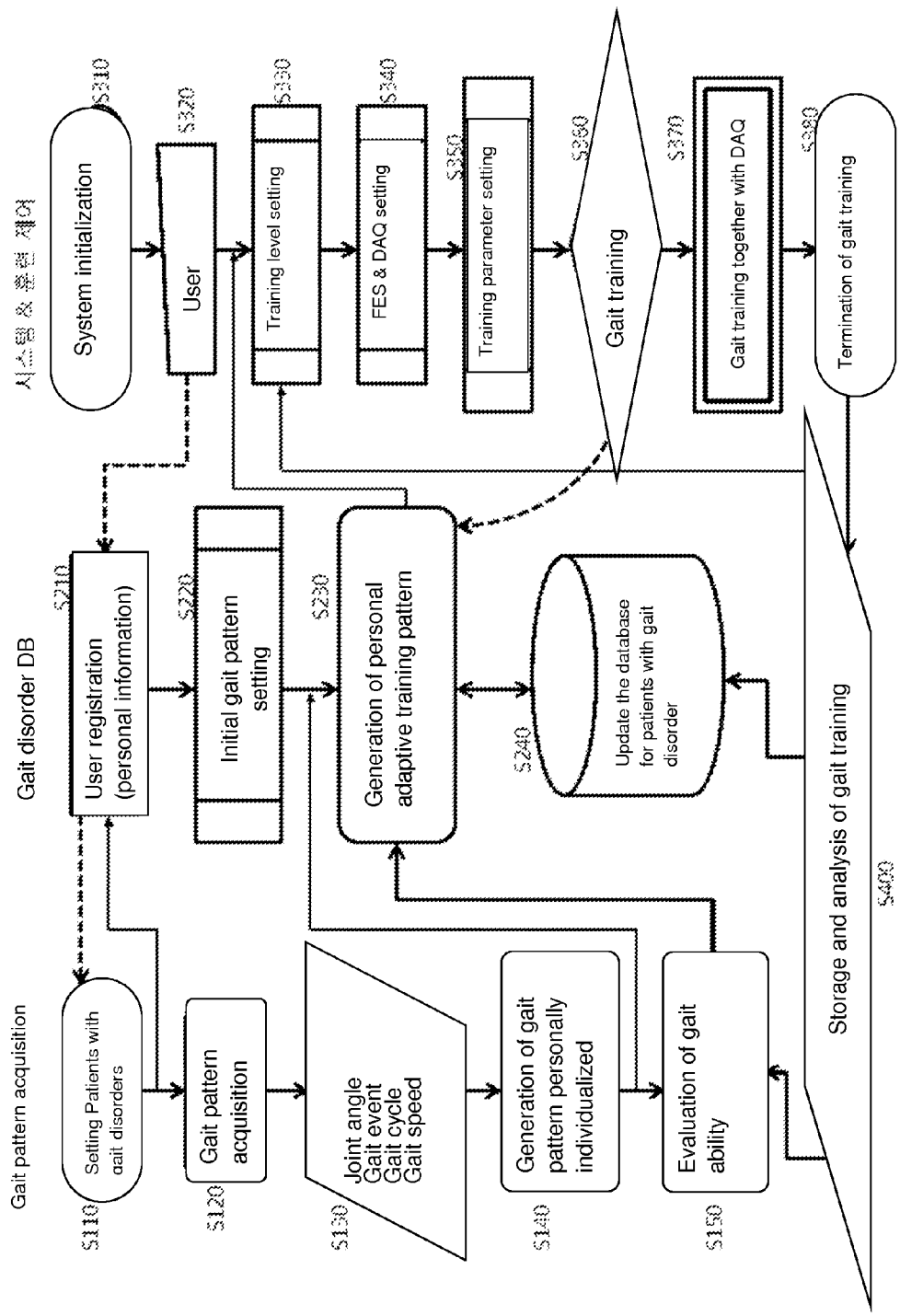
FIG. 11 is an explanation drawing for an overview of operating method of active robotic gait training system of the present invention.

FIG. 11 is an explanation drawing for an overview of operating method of the active robotic gait training system of the present invention.

As the step (S110) inputting the basic information of the patient with gait disorders, it sets the patient as the subject for gait training, and enters the basic information (personal information) of patients with gait disorders.

As the step (S120) collecting the gait pattern, it measures the gait of patients with gait disorders and collects the gait pattern.

As the step (S130) detecting the gait parameters, it detects the gait parameters related to the gait training, that is, it detects the joint angle, gait event, gait cycle and gait speed. The gait event includes the gait timing.

As the step (S140) producing the gait pattern of the training, it generates the gait pattern for gait training, by using the parameters detected at the step detecting the gait parameters. The gait pattern is the personally individualized gait pattern for gait training.

As the step (S150) evaluating the gait ability, it evaluates the gait ability by using the previously stored data.

The step (S110) inputting the basic information of the patient with gait disorders or the step (S150) evaluating the gait ability, can be the step of the gait pattern acquisition that analyzes the motions and collects the gait pattern.

The followings describe the steps to make database with detection or setting data by patients with gait disorders.

As the step (S210) loading the user registration information, it reads the basic information (personal information) of users of the gait training system who are patients with gait disorders.

As the step (S220) setting the initial gait pattern, it sets the initial gait pattern being used in the gait training system.

As the step (S230) generating the personal adaptive training pattern, it generates the personal adaptive training pattern, by using the step (S210) loading the user registration information, the step (S140) producing the gait pattern of the training, and the previously stored database for patients with gait disorders.

As the step (S240) updating the database, it stores and updates the generated personal adaptive training pattern information.

The step (S210) loading the user registration information or the step (S240) updating the database, can be the step making database by patients with gait disorders.

The followings describe the control based the system and the training.

As the system initialization step (S310), it initializes the system.

As the user search step (S320), it searches and recognizes the user.

As the step (S330) setting training level, it sets the training level (namely the training intensity level) of the training using training pattern.

For example, if it is set with 6 steps, the joint angle control of left and right knee joint units and left and right hip joint units of the gait training device (10), are divided into 6 steps based on the difference between normal gait and the patient gait.

As the step (S340) setting the FES sensor, it sets the stimulation speed and the stimulation location of the FES sensor, and sets the speed of data acquisition (DAQ).

As the step (S350) setting the training parameter, it sets the training parameter in the gait training device (10).

As the gait training simulation step (S360), it checks out the equipment operation situation by performing the gait training simulation with the gait training pattern being set only with the gait training device (10). Then, if a problem is found, it returns to the step (S230) generating the personal adaptive training pattern, and the training pattern is re-generated.

As the gait training step (S370), it performs the gait training and performs the data acquisition at the same time.

As the step (S400) analyzing the result of gait training, when the gait training is completed (S380), it stores and analyzes the result of gait training.

The data stored at the step (S400) analyzing the result of gait training, will be used henceforward in the step (S120) collecting the gait pattern and the step making database by patients with gait disorders.

In here, although the preferred embodiments of the present invention have been described, it will be understood by those skilled in the art that the present invention should not be limited to the described preferred embodiments, but various changes and modifications can be made within the sprit and scope of the present invention as defined by the appended claims.

INDUSTRIAL APPLICABILITY

The present invention relates to the active robotic gait training system in which is allowed more active gait training based on remaining gait ability of patients with gait disorders. It can be used for the gait training of patients with gait disorders in the rehabilitation hospitals.

What is claimed is:

1. A robotic gait training system, comprising:
a femoral support unit supporting a thigh of a patient;
a hip joint support unit supporting buttocks of the patient and a first end of the hip joint support unit being rotatably coupled with an upper part of the femoral support unit;
a lower leg support unit supporting a lower leg of the patient and rotatably coupled with a lower end of the femoral support unit;
an ankle support unit supporting an ankle of the patient, separated from the lower leg support unit and coupled to a lower part of the lower leg support unit, the ankle support unit extending downwards from the lower part of the lower leg support unit with a predetermined length;
a support fixing toe tip coupled to an upper end of the ankle support unit and the lower part of the lower leg support unit such that the support fixing toe tip is positioned at an ankle height of the patient in use;
a toe tip pad suspended from the support fixing toe tip and supporting and wrapping a forefoot of the patient;
a tilt sensor installed in the lower part of lower leg support unit or in the toe tip pad;
a first linear actuator operation unit coupled between the hip joint support unit and the femoral support unit and rotating the femoral support unit relative to the hip joint support unit, the first linear actuator operation unit including
a first load cell measuring a force applied in a hip joint support unit to lift the femoral support unit and having a first end fixed on the femoral support unit,
a first piston and cylinder of which a piston side is coupled to a second end of the first load cell and a cylinder side is fixed on the hip joint support unit
a first gear unit engaged with threads of the first piston and cylinder, and
a first servo motor rotating the first gear unit such that the first piston and cylinder make a linear motion,
a second linear actuator operation unit coupled between the femoral support unit and the lower leg support unit and rotating the lower leg support unit relative to the femoral support unit, the second linear actuator operation unit including;
a second load cell measuring a force applied in the knee joint support unit to lift the lower leg support unit and having a first end fixed on the lower leg support unit,
a second piston and cylinder of which a piston side is coupled to a second end of the second load cell and a cylinder side is fixed on the femoral support unit,
a second gear unit engaged with threads of the second piston and cylinder, and
a second servo motor rotating the second gear unit such that the second piston and cylinder make a linear motion,
a control unit controlling the robotic gait training system and generating a functional electric stimulation (FES) control signal to stimulate a plantarflexor or dorsiflexor of ankle joint by using a signal received from the tilt sensor; and
an FES unit stimulating the plantarflexor or dorsiflexor of ankle joint based on the FES control signal received from the control unit.

2. The robotic gait training system as claimed in claim 1, wherein the control unit generates a hip joint angle control signal and a knee joint angle control signal by using a slope signal received from the tilt sensor,
the first linear actuator operation unit receives the hip joint angle control signal from the control unit and rotates the femoral support unit based on the hip joint angle control signal, and
the second linear actuator operation unit receives the knee joint angle control signal from the control unit and rotates the lower leg support unit based on the knee joint angle control signal.

3. The robotic gait training system as claimed in claim 2, wherein the control unit estimates a gait cycle from the slope signal and generates the hip joint angle control signal based on the estimated gait cycle by using a previously stored hip joint operation pattern.

4. The robotic gait training system as claimed in claim 2, wherein the control unit estimates a gait cycle from the slope signal and generates the knee joint angle control signal based on the estimated gait cycle by using a previously stored knee joint operation pattern.

5. The robotic gait training system as claimed in claim 3, wherein the hip joint support unit is equipped with a first encoder to measure a rotated angle of the femoral support unit.

6. The robotic gait training system as claimed in claim 4, wherein the knee joint support unit is equipped with a second encoder to measure a rotated angle of the lower leg support unit.

7. The robotic gait training system as claimed in claim 5, wherein the control unit estimates the gait cycle from the slope signal and receives the hip joint angle control signal from the first encoder, and then generates the hip joint angle control signal based on the estimated gait cycle by using the previously stored hip joint operation pattern.

8. The robotic gait training system as claimed in claim 6, wherein the control unit estimates the gait cycle from the slope signal and receives the knee joint angle control signal from the second encoder, and then generates the knee joint angle control signal based on the estimated gait cycle by using the previously stored knee joint operation pattern.

9. The robotic gait training system as claimed in claim 2, wherein the femoral support unit, the hip joint support unit and the lower leg support unit form a robot-assisted gait training device for one leg and the robotic gait training system contains one pair of the robot-assisted gait training devices for left and right legs and contains a treadmill on which the patient who puts on one pair of the robot-assisted gait training devices does a gait training.

10. The robotic gait training system as claimed in claim 1, further comprising:
   a treadmill on which the patient does a gait training;
   a frame installed on a floor and over the treadmill;
   a pulley installed on the frame;
   a harness put on the patient;
   a rope installed on the harness;
   a counterweight installed on the frame and coupled with one end of the rope passing through the pulley.

11. The robotic gait training system as claimed in claim 1, further comprising:
   a femoral strap installed on the femoral support unit to couple the femoral support unit and the thigh of the patient;
   a lower leg strap installed on the lower leg support unit to couple the lower leg support unit and the lower leg of the patient; and
   an ankle strap installed on the ankle support unit to couple the ankle support unit and the ankle of the patient.

\* \* \* \* \*